(12) United States Patent
Hazebrouck

(10) Patent No.: US 7,431,723 B2
(45) Date of Patent: Oct. 7, 2008

(54) DEVICE AND METHOD FOR SEPARATION OF MODULAR ORTHOPAEDIC ELEMENTS

(75) Inventor: Stephen A. Hazebrouck, Winona Lake, IN (US)

(73) Assignee: Depuy Products, Inc., Warsaw, IN (US)

( * ) Notice: Subject to any disclaimer, the term of this patent is extended or adjusted under 35 U.S.C. 154(b) by 93 days.

(21) Appl. No.: 10/869,288

(22) Filed: Jun. 16, 2004

(65) Prior Publication Data
US 2005/0038441 A1    Feb. 17, 2005

Related U.S. Application Data

(62) Division of application No. 10/229,203, filed on Aug. 27, 2002, now Pat. No. 6,786,931.

(51) Int. Cl.
*A61B 17/28* (2006.01)
*A61B 17/00* (2006.01)

(52) U.S. Cl. .................. 606/99; 606/53; 606/86 R; 606/205; 606/207; 81/300; 81/415

(58) Field of Classification Search .............. 606/53, 606/86, 205–208, 99; 81/300, 415
See application file for complete search history.

(56) References Cited

U.S. PATENT DOCUMENTS

| | | | |
|---|---|---|---|
| 1,813,038 A | | 7/1931 | Erne |
| 3,263,535 A | * | 8/1966 | Zurcher ........................ 81/302 |
| 5,019,105 A | * | 5/1991 | Wiley ........................ 623/22.29 |
| 5,549,703 A | | 8/1996 | Daigle et al. |
| 6,000,686 A | * | 12/1999 | Yates .............................. 269/6 |
| 6,165,222 A | * | 12/2000 | Hoeppner et al. ......... 623/20.15 |
| 6,269,535 B1 | * | 8/2001 | McHugh et al. ................ 29/764 |
| 6,293,954 B1 | * | 9/2001 | Fogarty et al. .............. 606/205 |
| 6,412,375 B1 | | 7/2002 | Wang et al. |
| 6,458,022 B1 | * | 10/2002 | Folz ........................... 451/365 |
| 6,551,316 B1 | * | 4/2003 | Rinner et al. ................. 606/57 |
| 6,613,092 B1 | | 9/2003 | Kana et al. |
| 6,905,506 B2 | * | 6/2005 | Burbank et al. ............. 606/205 |
| 7,229,465 B2 | * | 6/2007 | Burbank et al. ............. 606/205 |
| 2003/0204267 A1 | | 10/2003 | Hazebrouck et al. |

* cited by examiner

*Primary Examiner*—Dave Willse
*Assistant Examiner*—Javier G Blanco

(57) ABSTRACT

A tool, system and method for separating connected orthopaedic components are disclosed. The system includes two orthopaedic components that are connected end to end. One of the orthopaedic components has a notch that receives a cam carried by the tool. The notch and cam are sized and shaped so that when the cam is turned, the cam forces the two components apart. The invention is particularly useful when Morse tapers are used to connect the components. The invention can be used with the modular orthopaedic implants as well as with modular trials used intraoperatively. The cam can be removably mounted on the tool.

3 Claims, 7 Drawing Sheets

DEVICE AND METHOD FOR SEPARATION OF MODULAR ORTHOPAEDIC ELEMENTS

CROSS REFERENCE TO U.S. UTILITY PATENT APPLICATION

This application is a Divisional Application based upon a U.S. Utility patent application, Ser. No. 10/229,203 entitled "DEVICE, SYSTEM AND METHOD FOR SEPARATION OF MODULAR ORTHOPAEDIC ELEMENTS" filed by Stephen A. Hazebrouck on Aug. 27, 2002, now U.S. Pat. No. 6,786,931, the complete disclosure of which is incorporated by reference herein.

BACKGROUND AND SUMMARY OF THE INVENTION

The present invention relates to a device or tool that can be used to separate modular elements that are connected by a Morse taper. More particularly, the invention relates to such a tool that can be used to disassemble modular orthopaedic elements that have Morse tapers. The invention also relates to a system and method for separating such modular orthopaedic elements, such as orthopaedic implants and orthopaedic trials.

Morse connections are those in which mating male and female ends of two elements are tapered to frictionally interlock when pressed or impacted together. Typical Morse tapers provide male and female ends that are conically or frustoconically shaped. The angle of the frustoconical taper is typically less than about 8°, and typically in the range of about 2-4°, which creates considerable friction to lock the male and female ends together.

Morse connections have been used in the orthopaedic field. U.S. Pat. No. 5,549,703 teaches that "It is known in the art to form a connection between two orthopaedic prosthetic components using a Morse taper or taper lock connection. One of the most common examples of such a connection is the neck of a hip stem that forms a connection with a correspondingly shaped socket in the ball of the femoral head component typically called the femoral head."

However, problems can arise with using a Morse taper to connect two orthopaedic components or elements. Although the connection is very strong, it is difficult to later separate the two elements without damaging the implant. Thus, it has been difficult to use Morse tapers to connect two orthopaedic elements or components that may later need to be separated. This difficulty renders it difficult to use Morse tapers for orthopaedic trials, and to use Morse tapers for modular components of orthopaedic implants.

The present invention addresses the need for a tool, system and method that effectively loosens a Morse connection between two orthopaedic components without damaging the components of the implant and while maintaining the advantages of a Morse connection. It should be understood that the present invention may be useful in separating orthopaedic elements connected through other connections as well.

In one aspect, the present invention addresses this need by providing a disassembly device for use in separating two orthopaedic components. The disassembly device includes a pair of handles pivotally connected. There is at least one cam on each handle. The cams are opposite to each other. The handles and cams are made of a material suitable for surgical use. The handles are sized and shaped to be manually operable.

In another aspect, the present invention addresses this need by providing an orthopaedic system. The system comprises first and second orthopaedic components and a disassembly tool. The second orthopaedic component is capable of being connected to the first orthopaedic component in a longitudinal end to end relationship. At least one of the orthopaedic components has an open-ended notch. The disassembly tool is used for separating the first and second orthopaedic components. The disassembly tool includes a cam. The notch is sized and shaped to receive the cam when the first and second orthopaedic components are connected. The cam is rotatable in the notch to cause relative longitudinal movement between the first and second orthopaedic components for separation of the first and second orthopaedic components.

In another aspect, the present invention addresses this need by providing a method of separating two connected orthopaedic components. Each of the orthopaedic components has a surface, and at least one of the orthopedic components has a notch open to a surface of the adjacent orthopaedic component when the two components are connected. The method includes inserting a cam in the notch and moving the cam in the notch so that the cam acts against the orthopaedic components to separate the components.

DETAILED DESCRIPTION OF THE ILLUSTRATED EMBODIMENT

Figure 1:
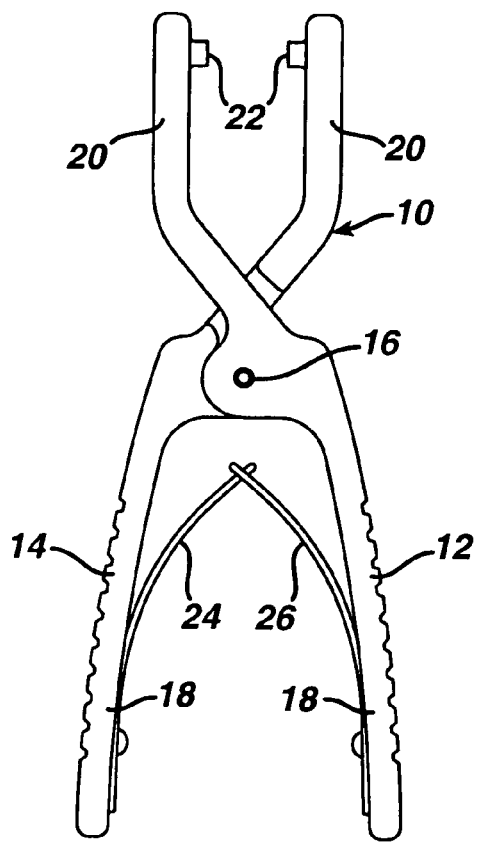
FIG. 1 is top plan view of a disassembly device for modular orthopaedic elements embodying the principles of the present invention.
Figure 2:
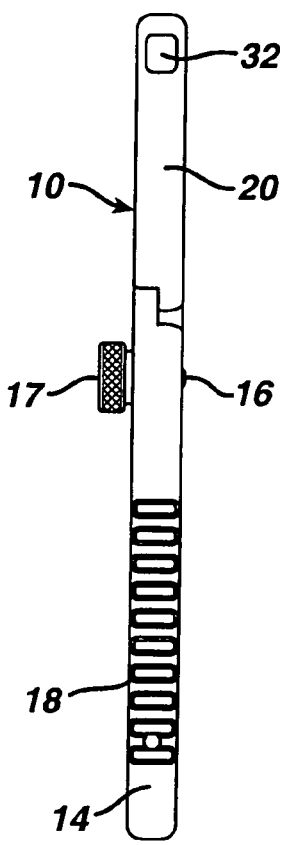
FIG. 2 is a side elevation of the disassembly device of FIG. 1.
Figure 3:
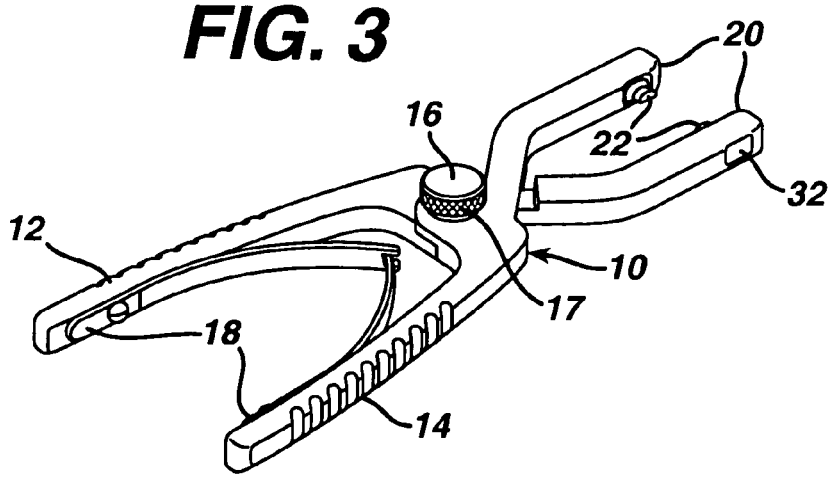
FIG. 3 is an isometric view of the disassembly device of FIGS. 1-2.
Figure 4:
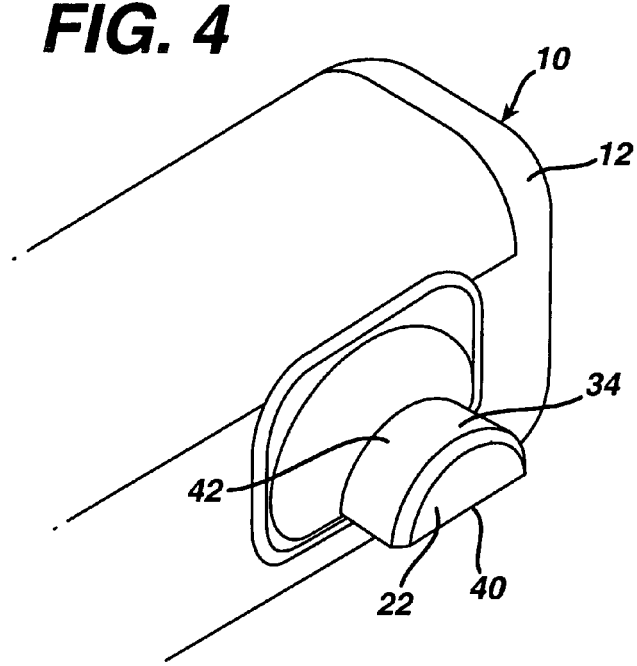
FIG. 4 is an enlarged isometric view of one end of one of the handle members of the disassembly device of FIGS. 1-4.
Figure 5:
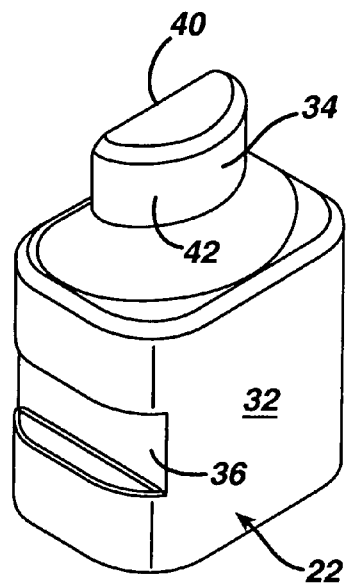
FIG. 5 is an isometric view of the cam member carried by one of the handle members.
Figure 6:
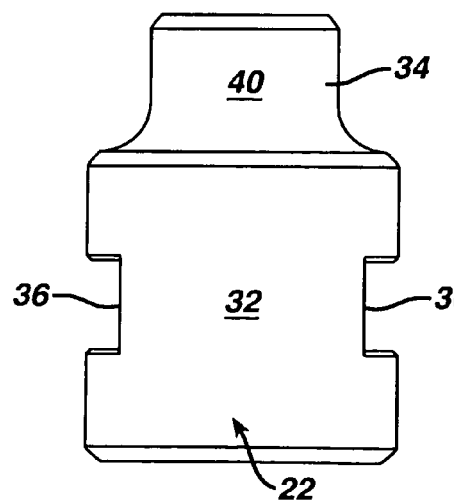
FIG. 6 is a front elevation of the cam member of FIG. 5.

An illustrative disassembly device or tool for the separation of modular orthopaedic components is illustrated in FIGS. 1-3 of the accompanying drawings, wherein like reference numbers are used for like parts. The illustrated disassembly device 10 is a hand-held instrument that can be used to separate a male-female friction lock, such as a Morse taper lock, between two orthopaedic components.

The illustrated disassembly device 10 provides a scissor-like or plier-like operation through two handles 12, 14 connected and crossing over each other at a pivotal connection 16 by a knob 17. Each illustrated handle 12, 14 has a grip end 18 and a cam-receiving end 20. A cam member 22 is received at each cam-receiving end 20 of the handle. A pair of spring members 24, 26 at the grip ends 18 of the handles bias the grip ends 18 of the handles 12, 14 apart.

Figure 9:
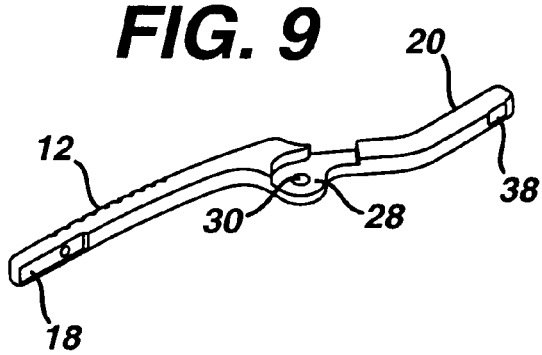
FIG. 9 is an isometric view of one of the handle members of the disassembly device of FIGS. 1-5.
Figure 10:
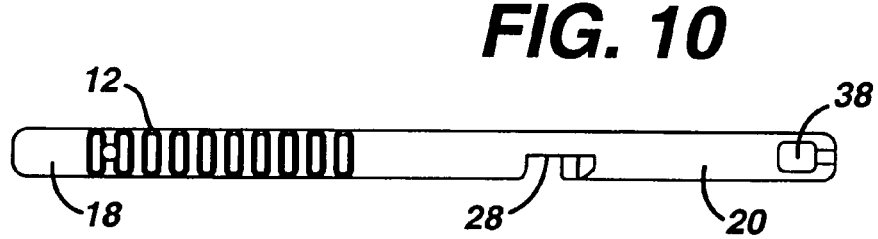
FIG. 10 is a side elevation of the handle member of FIG. 9.
Figure 11:
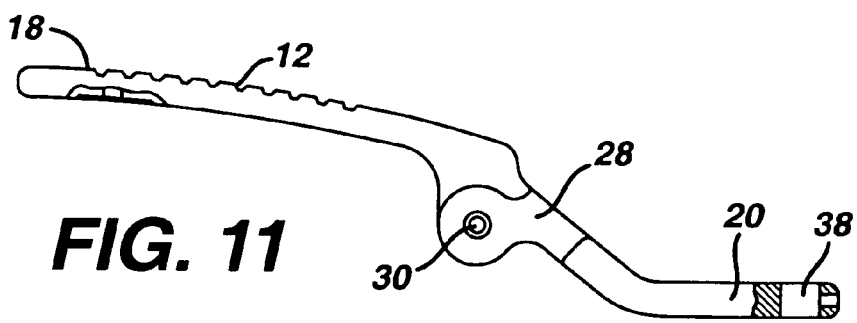
FIG. 11 is a top plan view of the handle member of FIGS. 8-9.

As shown in FIGS. 9-11, handle 12 has a notched central portion 28 connecting the grip end 18 and the cam-receiving end 20. The notched central portion 28 has a hole 30. As shown in FIG. 11, the grip end 18 and cam-receiving end 20 are offset from each other. The other handle 14 of the illustrated disassembly device has the same structure.

As shown in FIGS. 1 and 3, the two cam members 22 are opposed to each other and can be moved toward each other by squeezing the grip ends 18 of the two handles 12, 14 together. When the grip ends 18 of the handles 12, 14 are released, the spring members 24, 26 push the grip ends 18 of the handles apart, and the opposing cam members 22 also move apart. The illustrated handles 12, 14 are shaped accordingly.

The handles 12, 14, spring members 24, 26 and knob 17 can all be made out of standard medical grade materials. The material is one that is preferably capable of being sterilized repeatedly. As an example, 17-4 PH stainless steel can be used for these members of the tool. The components of the tool may be heat treated to, for example, H900 RC for 38 minutes. It should be understood that this material is identified for purposes of illustration only; the invention is not limited to any particular material unless expressly called for in the claims.

For the cam members 22, it may be desirable to use a material with greater fatigue properties than the material used for the remaining parts of the tool 10. For example, TRIM-RITE stainless steel, ASTM-A276-98B UNS 542010 may be used for the cams 22. This material is available from Carpenter Specialty Alloys, Carpenter Technology Corporation, of Reading, Pa. and other sources. This material has advantageous properties for the cams: it has substantially greater strength and fatigue properties compared to 17-4 PH stainless steel. Cams made out of this material should be able to be used repeatedly with little or no wear. It should be understood that this material is identified for purposes of illustration only; the invention is not limited to any particular material unless expressly called for in the claims.

All of the components of the tool 10 may be made using known methods. For example, the handle elements 12, 14 and cams 22 can be machined from stock material.

An example of a suitable structure for the cam members 22 is illustrated in FIGS. 4-8. As there shown, the cam members 22 may comprise discrete elements, each with a body 32 for mounting the cam member to one of the handles 12, 14 and a guide portion 34. Providing discrete cam members 22 is advantageous in that in the event of cam wear, the cam members can be replaced without replacing the entire tool.

Each cam body 32 includes a pair of grooves 36. To mount the cam 22 on one of the handles 12, 14, the cam 22 is slipped into a receiving slot 38 in the handle at the cam receiving end 20. A set screw (not shown) may then be threaded through a hole (not shown) in the tip of the handle and tightened into one of the grooves 36 on the cam body 32 to thereby hold the cam in place on the handle. It should be understood that this mounting design is provided for purposes of illustration only, and that the present invention is not limited to any particular mounting design unless expressly called for in the claims. In addition, the present invention is not limited to a design where the cams and the handles are discrete elements unless expressly called for in the claims.

Figure 7:
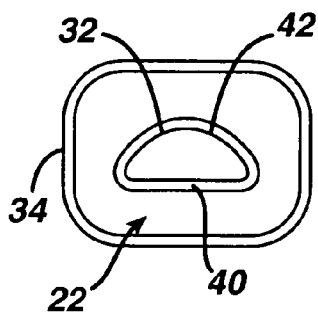
FIG. 7 is a top plan view of the cam member of FIGS. 5-6.
Figure 8:
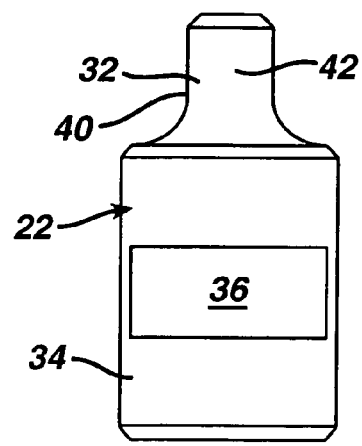
FIG. 8 is a side elevation of the cam member of FIGS. 5-7.

Each of the cam guide portions 34 in the illustrated embodiment comprises a half-moon shape, as best seen in the top plan view of FIG. 7. The illustrated guide portion 34 includes a flat surface 40 and a curved surface 42 joined at rounded corners. It should be understood that this shape of the cam guide portion is provided for purposes of illustration only, and that the present invention is not limited to any particular shape for the cam guide portion unless expressly called for in the claims.

Figure 12:
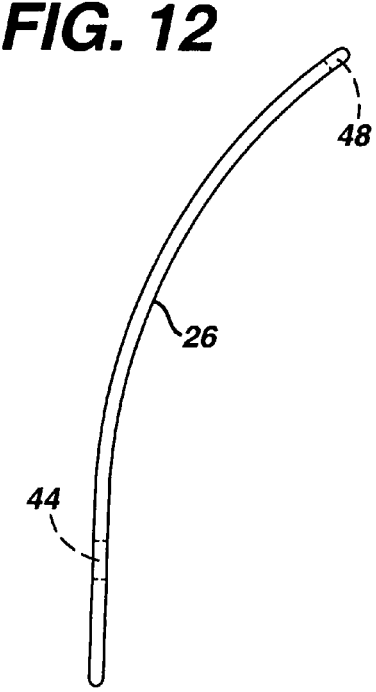
FIG. 12 is a side elevation of one of the spring members of the disassembly device of FIGS. 1-5.
Figure 13:
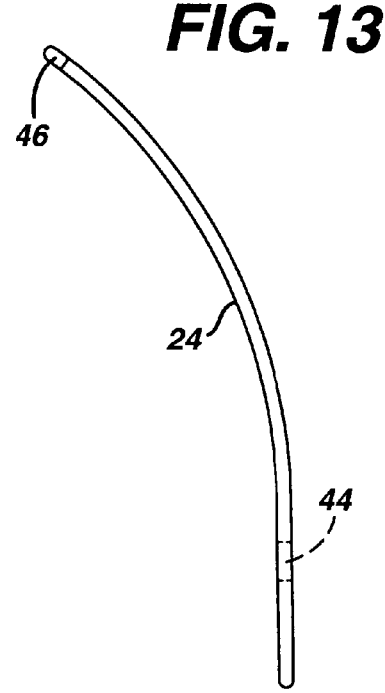
FIG. 13 is a side elevation of the other spring member of the disassembly device of FIGS. 1-5.
Figure 14:
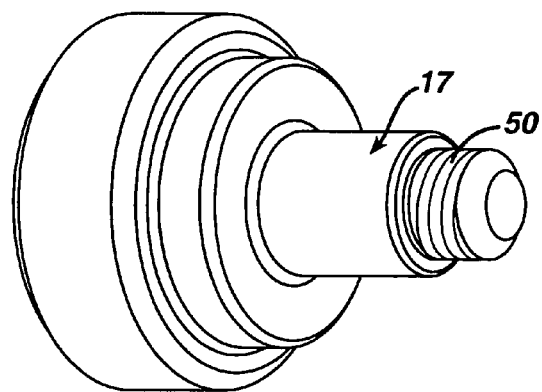
FIG. 14 is an isometric view of the knob of the disassembly device of FIGS. 1-5.

Suitable spring members 24, 26 are illustrated in FIGS. 12-13. In the illustrated embodiment, the spring members 24, 26 are discrete elements with holes 44 near one end and a mating tab 46 and slot 48 at the other ends. The spring members 24, 26 are assembled by slipping the tab 46 of one spring member into the slot 48 of the other spring member and slipped between the two handles 12, 14. Screws or the like may be used to secure the spring members 24, 26 to the handles 12, 14.

Generally, the spring members 24, 26 are mounted to the handles 12, 14 after the handles 12, 14 have been assembled together. To assemble the handles, after the cams 22 have been mounted to the handles, one handle is placed over the other with the notched central portion 28 of one handle 12 received in the notched central portion 28 of the other handle 14. The central holes 30 are aligned and the knob 17 is then slipped through the aligned holes 30 and threaded into one of the holes to secure the two handles together. Generally, only one of the handles (e.g. the left handle) will have a threaded hole to receive the threaded end 50 of the knob 17; the other hole will be large enough to allow relative rotation between the handles, in a scissor-like or plier-like fashion.

With the disassembly tool 10 so assembled, the cams 22 are positioned with the cam guide portions 34 opposite each other. By squeezing and releasing the handles at the grip ends 18, the cams can be moved toward and away from each other in a jaw or pincer-like manner.

Figure 15:
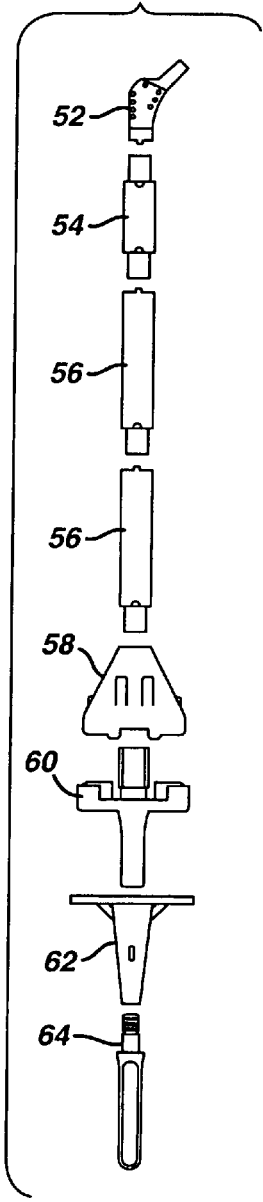
FIG. 15 is an exploded elevation view of the components of a proximal tibial replacement assembly and a total femoral replacement assembly with which the disassembly device can be used.
Figure 16:
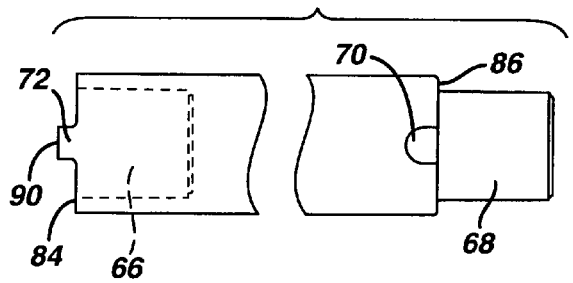
FIG. 16 is an elevation view of one modular orthopaedic component that can be used with the assemblies of FIG. 15.
Figure 17:
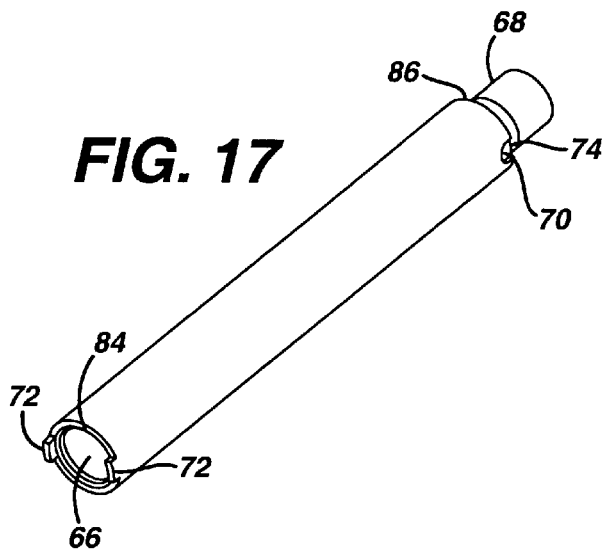
FIG. 17 is a perspective view of another modular orthopaedic component that can be used with the assemblies of FIG. 15.

The disassembly tool of FIGS. 1-14 may be used with modular orthopaedic components such as those illustrated in FIG. 15. The modular orthopaedic components may be like those described in "Modular Limb Preservation System", filed in the United States Patent and Trademark Office on Apr. 30, 2002 by Stephen A. Hazebrouck, Nick A. Deeter, Marc E. Ruhling, Joe William Ferguson and Mark B. Lester, Ser. No. 10/135,791, the complete disclosure of which is incorporated by reference herein. As there disclosed, and as illustrated in FIGS. 15-17, the modular components have mating male and female elements for connection between the components. The modular components with these male and female elements for connection can include, for example, a proximal femoral component 52, which has a female element at its distal end, or with a male connection element at its distal end (not shown); a segmental component with two male ends, such as that shown at 54 in FIG. 15; a segmental component with two female ends (not shown); one or more segmental components 56 with male and female ends; a distal femoral component, such as shown at 58 in FIG. 15, with a female end, as shown, or with a male end (not shown); and standard proximal tibial components, such as the tibial inset bearing, tibial tray and stem extension shown at 60, 62 and 64 in FIG. 15. The overall system shown in FIG. 15 can be used both for orthopaedic implants that are to be at least semi-permanently placed in the body, and for orthopaedic trials that are used intraoperatively by the surgeon to analyze a prospective implant before completing the implantation.

It should be understood that the components illustrated in FIG. 15 are provided by way of example only. The present invention can be used with other orthopaedic components used in other joints, such as at one of the extremeties, for example. The orthopaedic components, whether implants or trials, may be made of standard material and made in known processes.

In the system of orthopaedic components illustrated in FIG. 15, the male and female connecting elements comprise Morse taper connections. These Morse taper connections allow for the modular orthopaedic components to be press fit together, and are well known in the design of orthopaedic components as providing a strong and stable union between adjacent components. In the illustrated system, the female connecting element comprises a Morse taper bore 66 and the male connecting element comprises a Morse taper post 68. By way of example, each Morse taper bore 66 may have a depth of about 0.950 inches while the post 68 may have a length of about 0.800 inches. Both the bore 66 and post 68 are generally frustoconical in shape. Any typical angle for Morse tapers may be used, such as 2°24'35", for example. It should be understood that dimensions and angles are provided herein by way of example only; the present invention is not limited to any particular dimension or angle unless expressly called for in the claims.

It should be understood that although the present invention is particularly useful for separating orthopaedic components that are connected through a Morse taper, the invention is not limited to components with Morse tapers. Moreover, if there are other connections for the orthopaedic components other than male and female connecting elements, the present invention can also be expected to be useful in providing a mechanism for separating adjacent components using other connection mechanisms.

In the illustrated orthopaedic components, each of the illustrated male ends includes a pair of diametrically-opposed anti-rotation notches 70 and each of the illustrated female ends includes pair of diametrically-opposed anti-rotation tabs 72. Each of the notches 70 is sized to receive one of the tabs 72 therein when the two components are connected together. Thus, the interdigitation of the tabs 72 and notches 70 prevent relative rotation between the connected components.

Figure 17A:
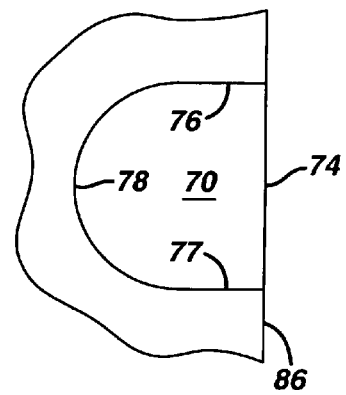
FIG. 17A is an enlarged view of one of the notches of the modular orthopaedic components of FIG. 16.
Figure 18:
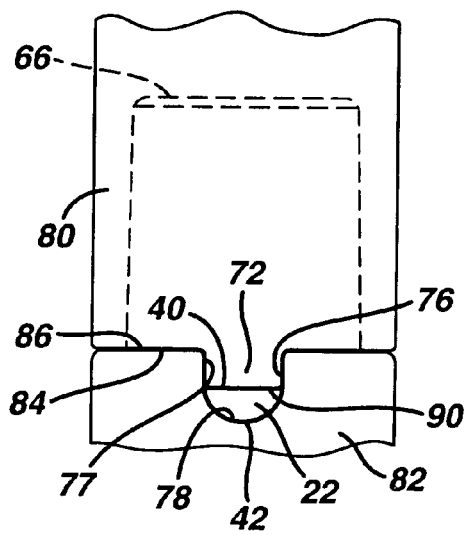
FIG. 18 is an enlarged elevation view showing male and female orthopaedic components connected by Morse taper elements, shown with the cam of the disassembly device received in the anti-rotation notch formed in one of the orthopaedic elements.

Each of the illustrated notches 70 is of similar shape, and it should be understood that the following description applies to all of the notches of the illustrated orthopaedic system. As shown in FIG. 17A, each notch has an open end 74, two spaced substantially parallel side edges 76, 77 and a curved edge 78 opposite the open end 74. The distance between the two spaced parallel side edges 76, 77 is slightly greater than the width of the tab 72, and the lengths of the two spaced parallel side edges 76 are generally the same as the height of the tab 72. Thus, the shape of the portion of the notch near the open end 74 corresponds with the shape of the tab 72, so that the tab mates with the portion of the notch near the open end to serve the anti-rotation function. However, the notch is larger than the tab 72, and is sized and shaped so that the cam guide surface 34 of one cam 22 can also be received within the notch 22 when the two orthopaedic components are connected, as shown in FIG. 18. Thus, the notch 70 in this embodiment is shaped to mate with both the tab 72 and the cam 22 simultaneously.

Figure 19:
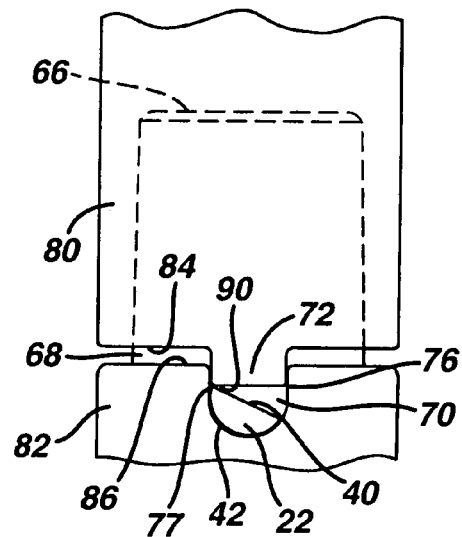
FIG. 19 is a view of the male and female orthopaedic components of FIG. 18 shown with the cam element of the disassembly tool of the present invention in place in the anti-rotation notch and turned to push against the anti-rotation tab to separate the male and female components.
Figure 20:
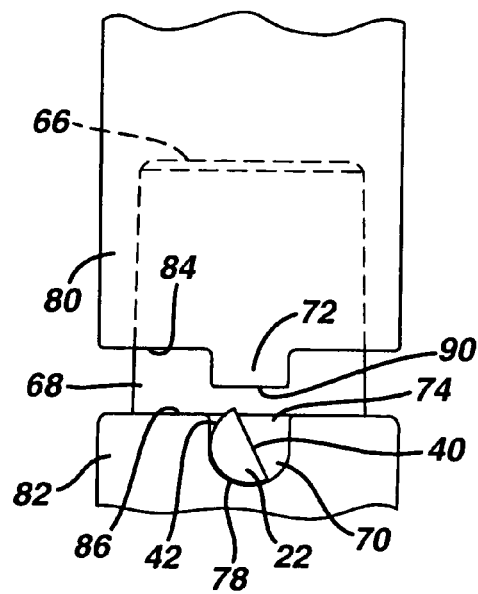
FIG. 20 is a view of the male and female orthopaedic components of FIGS. 18-19 shown with the cam element of the disassembly tool of the present invention in place in the anti-rotation notch and with the male and female components fully separated.

In FIGS. 18-20, the first orthopaedic component is shown at 80 and the second orthopaedic component is shown at 82. The two orthopaedic components 80, 82 have a planar edges 84, 86 that are juxtaposed when the orthopaedic components are connected, as shown in FIG. 18. As shown in FIG. 17A, the two parallel portions 76, 77 of the notch edge extend from the planar edge 86 to the curved portion 78. As shown in FIGS. 18-20, the anti-rotation tab 72 extends beyond the planar edge 84 of the first orthopaedic component 80.

To separate the components after they have been connected, with the Morse post 68 received in the Morse opening 66, the jaws of the tool 10 are aligned with the open portions of the notches 70. The tool 10 is squeezed bringing the cams 22 into position in the notches 70, as shown in FIG. 18, with the flat surface 40 of the cam 22 against the planar edge 90 of the tab 72 and the curved surface 42 of the cam against the curved edge 78 of the notch 70. The tool 10 is then rotated to cause the cams 22 to rotate as shown in FIG. 19. As the cams rotate, they push against the planar edge 90 of the tab 72, and the rotational movement of the cams is translated to relative longitudinal movement of the two orthopaedic components 80, 82. The two orthopaedic components 80, 82 separate, as shown in FIGS. 19-20 as the tool 70 is turned, and the frictional engagement of the Morse taper elements 66, 68 is broken, allowing for the two orthopaedic components 80, 82 to be manually separated. All of this is accomplished without damaging the orthopaedic components 80, 82, and without compromising the strength of the connection between these components.

Figure 21:
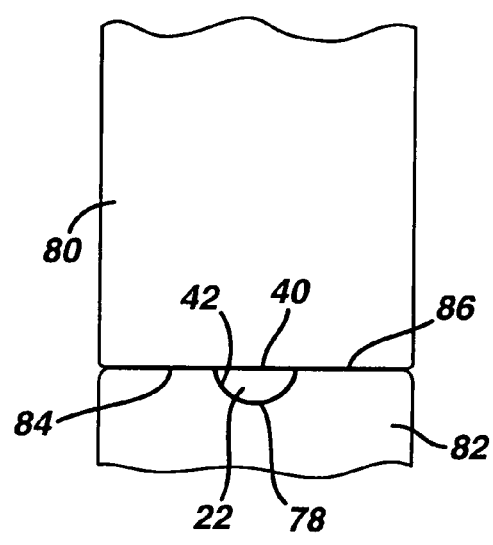
FIG. 21 is an enlarged elevation view showing male and female orthopaedic components without anti-rotation tabs, the two components connected by Morse taper elements, shown with the cam of the disassembly device received in the notch formed in one of the orthopaedic elements.
Figure 22:
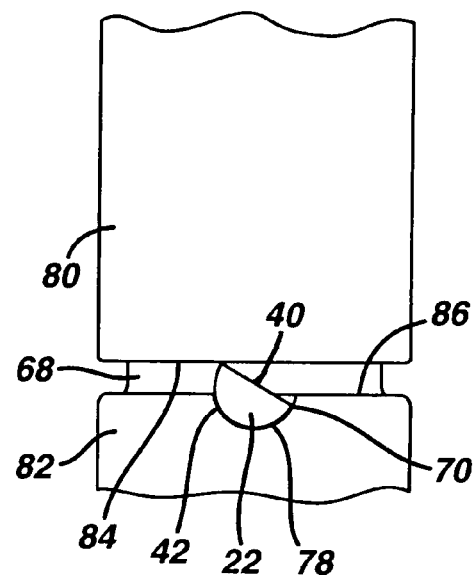
FIG. 22 is a view of male and female orthopaedic components of FIG. 21, shown with the cam element of the disassembly tool of the present invention in place in the notch and turned to push against the end surface of the adjacent orthopaedic component to separate the male and female orthopaedic components.
Figure 23:
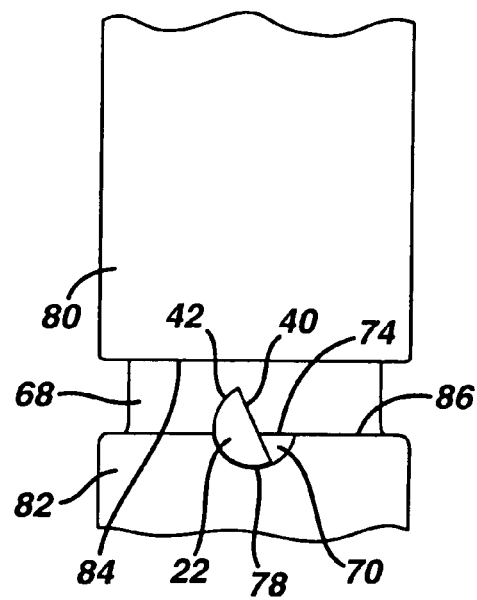
FIG. 23 is a view of the male and female orthopaedic components of FIG. 22 shown with the cam element of the disassembly tool of the present invention in place in the notch and with the male and female components fully separated.

It should be understood that the present invention can also be used with orthopaedic components where there is no anti-rotation tab 72, or where there are separate notches for the anti-rotation tab and for the cam. In the embodiment shown in FIGS. 21-23, there is no anti-rotation tab shown, although one could be provided at a separate location and with a separate notch. In the embodiment of FIGS. 21-23, like reference numbers have been used for like parts. In this embodiment, instead of acting against the planar edge of the tab, the cam 22 acts directly against the planar edge 84 of the component 80 to separate the two orthopaedic components.

It should be understood that various modifications and additions can be made to the above-described embodiment without departing from the invention. For example, instead of using a scissor-like tool as illustrated, a C-clamp type of tool, with opposing cams that are movable toward and away from each other through use of another mechanism, such as a screw, could be used. It may be possible to construct a tool and system utilizing only a single cam, or with more than two cams as illustrated. Various other modifications and additions can be made, and are intended to fall within the scope of the claims unless the claims expressly call for a specific construction.

I claim:

1. A disassembly device for use in separating two orthopaedic components, the disassembly device comprising:
   a pair of one-piece handles pivotally connected, each handle having first and second ends;
   an edge defining a slot in one handle and an edge defining a slot in the other handle, the slots being opposite to each other and spaced from the ends of the handles, each slot having a length, a width and a depth;
   a pair of cams, each cam having a body portion and a guide portion;
   the body portion of one cam being received in the slot in one handle and the body portion of the other cam being received in the slot in the other handle, the guide portion of each cam being exposed;
   the slots and the body portions of the cams being sized and shaped to limit relative rotation between the cams and the handles;
   the body portion of each cam comprising a first surface, a second surface spaced from the first surface and a third surface connecting the first and second surfaces, the distance between the first surface and second surface defining the height of the body portion, the first surface having a length in one direction and a width in an opposite direction;
   the guide portion of each cam comprising a curved surface with two ends, a planar surface extending between the ends of the curved surface, and an end surface perpendicular to the planar surface, the end surface having a straight edge and a curved edge, the curved surface and planar surface of the guide portion extending from the first surface of the body portion;
   the guide portion of each cam having a maximum length between the two ends of the curved surface, the maximum length of the guide portion being parallel to the length of the body portion, a maximum width between the planar surface and the curved surface, the maximum width of the guide portion being parallel to the width of body portion, and a maximum height between the end surface and the first surface of the body portion, the maximum height of the guide portion being parallel to the height of the body portion;

wherein:
   the maximum length of the guide portion is less than the length of the first surface of the body portion and less than the length of the slot with which the cam is associated;
   the maximum width of the guide portion is less than the width of the first surface of the body portion and less than the width of the slot with which the cam is associated;
   the maximum height of the guide portion is less than the height of the body portion;
   the entire body portion of each cam is positioned between the first and second ends of the handle with which the cam is associated;
   substantially all of the body portion of each cam is received in the slot with which the cam is associated;
   the entire guide portion of each cam is positioned to overlie the body portion when viewed in a top plan and a side elevational view;
   no part of the guide portion of each cam extends beyond the body portion when viewed in a top plan and side elevational view;
   the handles and cams are made of a material suitable for surgical use;
   the handles are sized and shaped to be manually operable;
   the guide portion of each cam is in a fixed orientation with respect to the body portion of the cam and the associated handle;
   the two cams are movable toward and away from each other through pivoting of the handles; and
   the handles are pivotable to a position wherein the end surfaces of the cams face each other and are substantially parallel to each other.

2. The disassembly device of claim 1 wherein the cams have greater fatigue properties than the handles.

3. The disassembly device of claim 1 wherein each cam is removably mounted on each handle.

* * * * *